United States Patent [19]

Itoh

[11] Patent Number: 5,449,848
[45] Date of Patent: Sep. 12, 1995

[54] DEHYDROGENATION PROCESS

[75] Inventor: Naotsugu Itoh, Tsukuba, Japan

[73] Assignee: Agency of Industrial Science and Technology, Tokyo, Japan

[21] Appl. No.: 764,295

[22] Filed: Sep. 23, 1991

Related U.S. Application Data

[63] Continuation of Ser. No. 470,466, Jan. 26, 1990, abandoned.

[30] Foreign Application Priority Data

Jun. 13, 1989 [JP]  Japan ................................. 1-151224

[51] Int. Cl.$^6$ ............................................. C07C 5/367
[52] U.S. Cl. ................... 585/430; 585/654; 95/55; 95/56
[58] Field of Search ............. 585/430, 654; 55/16

[56] References Cited

U.S. PATENT DOCUMENTS

| | | | |
|---|---|---|---|
| 1,685,759 | 9/1928 | Walter | 423/468 |
| 3,849,076 | 11/1974 | Gryaznov et al. | 422/149 |
| 4,132,668 | 1/1979 | Gryaznov et al. | 502/4 |
| 4,713,234 | 12/1987 | Weirich et al. | 423/648.1 |
| 4,810,485 | 3/1989 | Marianowski et al. | 423/648.1 |
| 4,891,464 | 1/1990 | Staggs | 585/654 |

OTHER PUBLICATIONS

Itoh, *J. Chem. Engineering of Japan*, 23, 1, pp. 81–87 (1990).
Gryaznov, *Consultants Bureau*, pp. 564–568 (1971).
Itoh, *Aiche Journal*, 33, 9, pp. 1576–1578 (1987).
Messungen et al, *Zeitschrift fur Physikalische Chemie Neue Folge*, Bd. 56, S. 133–154 (1967).
Itoh et al, *Int'l. J. of Hydrogen Energy*, 9, 10, pp. 835–839 (1984).
Itoh et al, *Int'l. Chem. Engineering*, 25, 1, pp. 138–142 (1985).
Itoh et al, *Sekiyu Gakkaishi*, 28, 4, pp. 323–327 (1985).
Kameyama et al, *Ind. Eng. Chem. Fundam.*, 20, pp. 97–99 (1981).
Nagamoto et al. *Chem. Eng. Commun.*, 34, pp. 315–323 (1985).
Raymont, *Hydrocarbon Processing*, pp. 139–142 (1975).
Sieverts et al, *Z. Physik. Chem.*, 34, p. 158 (1936).
*Merck Index*, 1976, p. 1146, right column, compound No. 8657.
*J. Japan Petrol Inst.*, 26, (1), 24–30 (1983), Tables 2, 3 and 4.

*Primary Examiner*—Sharon A. Gibson
*Assistant Examiner*—Nhat D. Phan
*Attorney, Agent, or Firm*—Armstrong, Westerman, Hattori, McLeland & Naughton

[57] ABSTRACT

A dehydrogenation apparatus comprising a dehydrogenation reaction chamber and a hydrogen combustion chamber adjoining to the dehydrogenation chamber through a hydrogen-permeable membrane, wherein the dehydrogenation reaction chamber has a tube for introducing a material to be dehydrogenated and a tube for discharging a dehydrogenation product, while the hydrogen combustion chamber has a tube for introducing oxygen or an oxygen-containing gas and a tube for discharging a hydrogen combustion gas, and the dehydrogenation reaction chamber and hydrogen combustion chamber are covered with a heat-insulating material.

3 Claims, 2 Drawing Sheets

DEHYDROGENATION PROCESS

This is a continuation, of application Ser. No. 07/470,466 filed Jan. 26, 1990, now abandoned.

BACKGROUND OF THE INVENTION

The present invention relates to a dehydrogenation apparatus.

The dehydrogenation reaction is accompanied by extensive heat absorption, and from the thermodynamical viewpoint, a higher reaction temperature results in a more advantageous dehydrogenation reaction.

On an industrial scale, the dehydrogenation reaction is generally carried out at a temperature of 550° to 650° C., and this reaction is a typical instance of large-energy-consumption type chemical processes. A large quantity of heat energy should be supplied to a reactor for maintaining a high temperature and ensuring much reaction heat. Accordingly, various contrivances have been made on the conventional dehydrogenation reaction apparatuses for overcoming this defect. For example, there are adopted a method in which the reactor is divided into a plurality of zones and a reheating zone is disposed in the intermediate portion of the reactor to prevent the fall of the reaction temperature, and a method in which a heating tube is directly arranged in a reaction layer. In the dehydrogenation reaction, in principle, the equilibrium reaction ratio is low, and therefore, in the conventional apparatus, it is necessary to dispose a special device for separating the unreacted starting material from the product. Furthermore, supply of a heat energy is indispensable for preventing the fall of the temperature of the reaction layer accompanying the dehydrogenation.

SUMMARY OF THE INVENTION

It is a primary object of the present invention to provide a dehydrogenation apparatus in which hydrogen obtained by the dehydrogenation reaction is utilized as the heat energy source.

A second object of the present invention is to provide a dehydrogenation apparatus in which the dehydrogenation can be carried out at a conversion of 100%.

In accordance with the present invention, these objects can be attained by a dehydrogenation apparatus comprising a dehydrogenation reaction chamber and a hydrogen combustion chamber adjoining to the dehydrogenation chamber through a hydrogen-permeable membrane, wherein the dehydrogenation reaction chamber has a tube for introducing a material to be dehydrogenated and a tube for discharging a dehydrogenation product, while the hydrogen combustion chamber has a tube for introducing oxygen or an oxygen-containing gas and a tube for discharging a hydrogen combustion gas, and the dehydrogenation reaction chamber and hydrogen combustion chamber are covered with a heat-insulating material.

DETAILED DESCRIPTION OF THE PREFERRED EMBODIMENT

Figure 1:
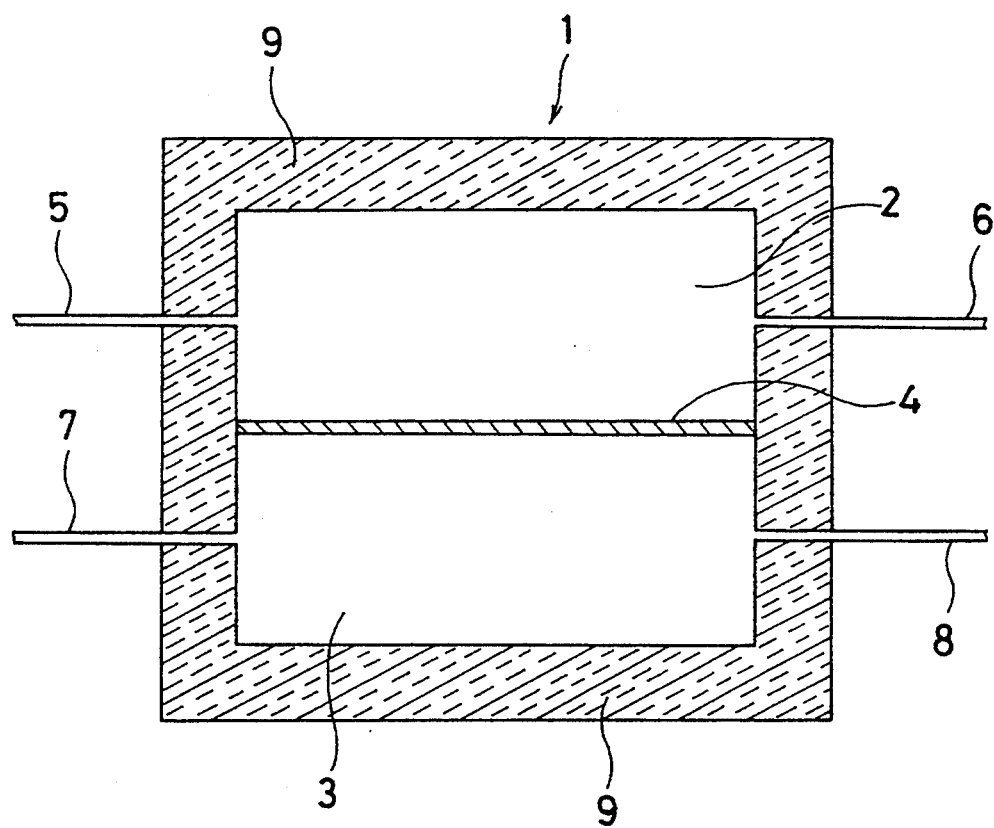
FIG. 1 is a diagram illustrating an embodiment of the apparatus of the present invention.

The dehydrogenation apparatus of the present invention will now be described in detail with reference to the embodiment illustrated in FIG. 1.

The dehydrogenation apparatus 1 of the present invention comprises a dehydrogenation reaction chamber 2 and a hydrogen combustion chamber 3 which adjoin to each other through a hydrogen-permeable membrane 4 interposed therebetween.

A tube 5 for introducing a starting material to be dehydrogenated and a tube 6 for discharging a dehydrogenation product are arranged in the dehydrogenation reaction chamber 2, and a tube 7 for introducing oxygen or an oxygen-containing gas and a tube 8 for discharging a hydrogen combustion gas are arranged in the hydrogen combustion chamber 3.

The dehydrogenation reaction chamber 2 and hydrogen combustion chamber 3 are covered with a heat-insulating material 9 so that egress and ingress of heat are inhibited.

The arrangement or shape of the dehydrogenation reaction chamber 2 and hydrogen combustion chamber 3 is not particularly critical, so far as they adjoin to each other through the hydrogen-permeable membrane 4.

As the hydrogen-permeable membrane 4, there can be used a membrane of a hydrogen-permeable material such as palladium, a palladium-gold alloy, a palladium-silver alloy, a palladium-nickel alloy, a palladium-rare earth metal alloy or the metals platinum, titanium, nickel, iron or copper, or a porous ceramic membrane or porous metal membrane having a coating of a hydrogen-permeable material as mentioned above, formed on the surfaces thereof, especially the surface opposed to the hydrogen combustion chamber.

The interiors of the dehydrogenation reaction chamber 2 and hydrogen combustion chamber 3 may be vacant. Alternatively, the chambers 2 and 3 may be filled with inert solid particles a dehydrogenation catalyst or a hydrogen-oxidizing catalyst. The selection can be made according to the target performances (such as reaction results or heat transfer characteristics) of the apparatus.

The functions of the dehydrogenation apparatus of the present invention having the above-mentioned structure will now be described.

At first, a starting material to be dehydrogenated is supplied into the dehydrogenation reaction chamber 2 through the introducing tube 5. The dehydrogenation reaction chamber 2 is filled with a dehydrogenation catalyst and is heated to a predetermined temperature.

The dehydrogenation reaction is thus caused in the dehydrogenation reaction chamber 2, and hydrogen is formed. This hydrogen is allowed to permeate through the hydrogen-permeable membrane 4 because of a difference in the hydrogen partial pressure between the dehydrogenation reaction chamber 2 and the hydrogen combustion chamber 3, and the hydrogen is transferred into the hydrogen combustion chamber 3. At this point, a kind of catalytic reaction is caused on the surface of the membrane opposed to the hydrogen combustion chamber 3. This is because the hydrogen-permeable membrane also performs a function as a good catalyst for oxidation reaction of hydrogen.

Accordingly, the hydrogen which has passed through the hydrogen-permeable membrane 4 reacts with oxygen supplied into the hydrogen combustion chamber 3 from the oxygen or oxygen-containing gas introducing tube 7 mainly on the surface of the hydrogen-permeable membrane 4 opposed to the hydrogen combustion chamber 3, and the hydrogen is thus converted to water vapor, which is discharged outside the apparatus through the hydrogen combustion gas discharging tube 8.

By consuming hydrogen in the hydrogen combustion chamber 3 through the oxidation reaction in the above-mentioned manner, hydrogen formed in the dehydrogenation reaction chamber 2 is continuously and completely consumed.

Furthermore, in the apparatus of the present invention, the dehydrogenation reaction accompanied by extensive heat absorption and the oxidation reaction of hydrogen accompanied by extensive heat generation are simultaneously advanced on both the sides of the interposed partition wall, and the reaction system is thermally insulated from the outside. Accordingly, no dissipation of heat to the outside is caused and only the transfer of heat from the hydrogen combustion chamber 3 where the temperature is relatively elevated by heat generation to the dehydrogenation reaction chamber 2 where the temperature is relatively lowered by heat absorption is caused.

As a result, by the elevation of the dehydrogenation reaction temperature by this adiabatic transfer of heat to the dehydrogenation reaction chamber 2 from the hydrogen combustion chamber 3, the dehydrogenation reaction is further advanced highly efficiently and is brought to completion.

The above-mentioned dehydrogenation apparatus of the present invention can be applied to various known dehydrogenation reactions. For example, the apparatus of the present invention can be utilized for the dehydrogenation reaction of hydrocarbon source materials such as ethylbenzene, methanol, butane, butene and cyclohexane, and the dehydrogenation reaction of inorganic hydrogen compounds such as hydrogen sulfide or hydrogen iodide.

According to the present invention, hydrogen formed by the dehydrogenation reaction is continuously removed from the dehydrogenation reaction chamber through the hydrogen-permeable membrane, and heat generated by the oxidation reaction in the hydrogen combustion chamber can be supplied to the dehydrogenation reaction chamber without any loss because the chambers are covered with heat-insulating material. Therefore, when the apparatus of the present invention is used, the dehydrogenation reaction having a low equilibrium reaction ratio is prominently promoted and a conversion of 100% can be attained. Accordingly, any post-treatment equipment for separating the products from the unreacted starting material, which is indispensable in the conventional process, becomes unnecessary. Moreover, an energy for heating a heating medium (mainly, superheated steam) to be supplied for preventing the fall of the temperature of the reaction layer due to the dehydrogenation reaction becomes unnecessary.

The analysis of the dehydrogenation reaction in the apparatus of the present invention has been carried out on the following prerequisites:

The dehydrogenation reaction chamber 2 is filled with a catalyst and a metallic palladium membrane is used as the hydrogen-permeable membrane 4; and The formation of benzene by the dehydrogenation of cyclohexane is carried out by feeding starting cyclohexane into the dehydrogenation reaction chamber 2 and simultaneously supplying an oxygen-containing gas into the hydrogen combustion chamber 3, each under atmospheric pressure at 200° C.

Figure 2A:
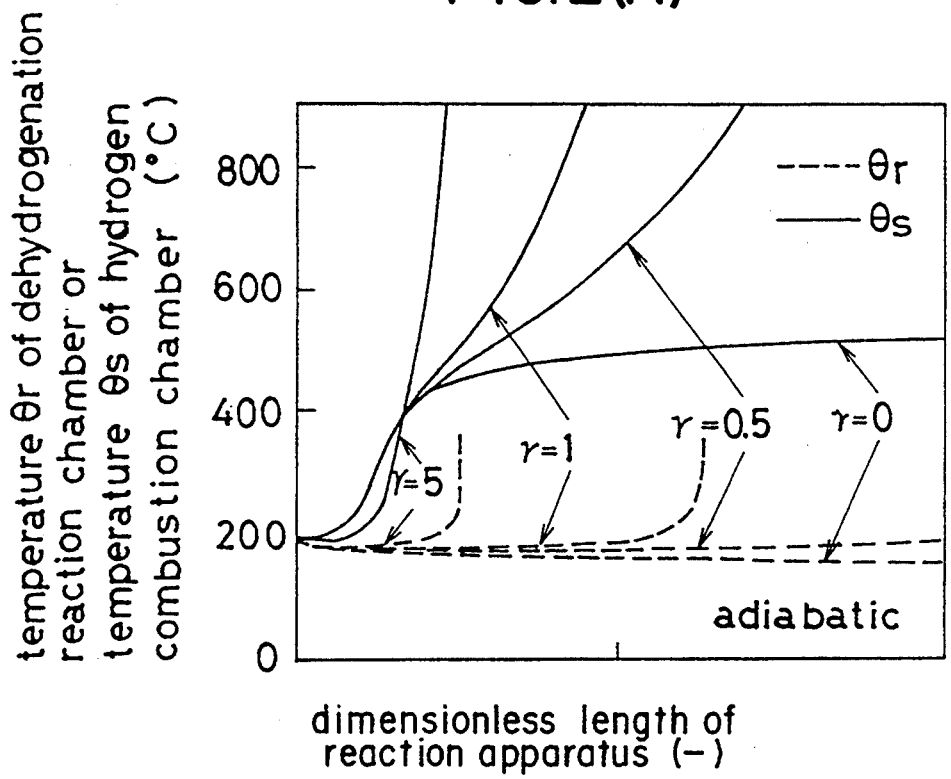
FIG. 2(A) is a graph of temperature of the dehydration reaction and the temperature of the hydrogen combustion chamber against the dimensionless length of the reaction apparatus of the present invention.
Figure 2B:
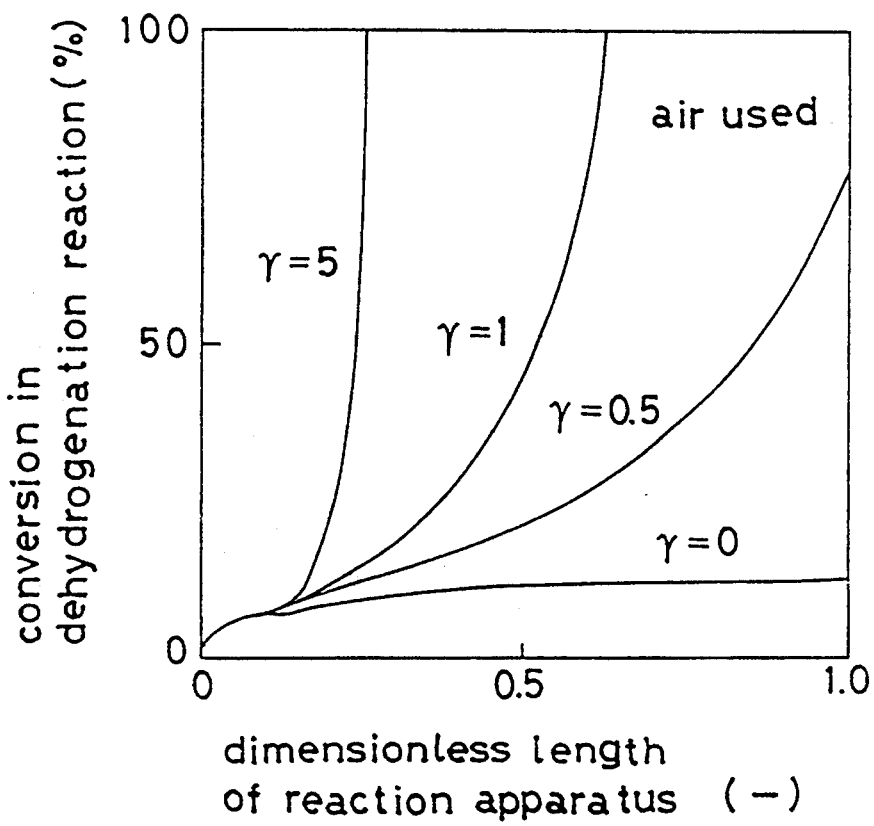
FIG. 2(B) is a graph of percent conversion of the dehydrogenation reaction against the dimensionless length of the reaction apparatus of the present invention.

An example of the result of the calculation is shown in FIG. 2.

Air (having an oxygen concentration of 20.95%) is used as the oxygen-containing gas, and the $\gamma$ (gamma) value, that is, the dimensionless number represented by (heat transfer coefficient × membrane area) × (specific heat of starting material × feed speed of starting material), is used as the calculation parameter. The result of the calculation made with this dimensionless number varied is shown in FIG. 2. In case of $\gamma = 0$, that is, in the case where the heat transfer coefficient is zero, heat generated in the hydrogen combustion chamber 3 is not transferred to the dehydrogenation reaction chamber 2. This case corresponds substantially to the case where no heat is replenished in the conventional reaction apparatus. In this case, the temperature of the reaction layer is not elevated and the conversion is about 10% at the highest, as is obvious from FIG. 2.

As the $\gamma$ value is gradually increased to 0.5, 1 or 5, the elevation of the temperatures in the dehydrogenation reaction chamber 2 and hydrogen combustion chamber 3 becomes vigorous and the speed of the elevation of the temperature increases. This is due to the fact that the permeating hydrogen is reacted with oxygen in the hydrogen combustion chamber 3 to generate heat and this heat is transferred to the dehydrogenation reaction chamber 2 to heat the dehydrogenation reaction layer. This elevation of the dehydrogenation reaction temperature results in an increase of the reaction speed and also an increase of the amount of generated hydrogen. Accordingly, the amount of permeating hydrogen is increased and the quantity of heat generated in the hydrogen combustion chamber 3 is increased. For this reason, the temperature is elevated at a more and more increasing rate. Correspondingly, the rise rate of the conversion curve increases and the length (size) of the reaction apparatus required for the completion of the reaction can be diminished.

What is claimed is:

1. A process for dehydrogenation, comprising:
    performing a dehydrogenation reaction in one of two reaction zones arranged adjacent to each other through a hydrogen-permeable membrane, thereby producing a dehydrogenation product and hydrogen,
    separating said hydrogen from said dehydrogenation product by discharging said dehydrogenation product from said one of two reaction zones and, at the same time, permitting the hydrogen obtained to enter the other reaction zone through said hydrogen-permeable membrane;
    introducing oxygen or oxygen-containing gas into said other reaction zone and subjecting the hydrogen to combustion in said other reaction zone; and
    discharging the resultant combustion product from said other reaction zone and, at the same time, supplying at least a portion of the heat generated by said combustion to said dehydrogenation reaction.

2. The process of claim 1, wherein the hydrogen-permeable membrane is a member selected from the group consisting of a membrane of a hydrogen-permeable metal, a porous ceramic membrane having a surface coated with a hydrogen-permeable metal and a porous metal membrane having a surface coated with a hydrogen-permeable metal.

3. The process of claim 2, wherein the hydrogen-permeable metal is selected from the group consisting of palladium, a palladium-gold alloy, a palladium-silver alloy, a palladium-nickel alloy, a palladium-rare-earth metal alloy, titanium, nickel, iron and copper.

* * * * *